United States Patent [19]

Sarbach

[11] Patent Number: 5,628,324

[45] Date of Patent: May 13, 1997

[54] AUTONOMOUS SYSTEM FOR MEASURING, PROCESSING AND TRANSMITTING ESSENTIALLY PHYSIOLOGICAL PARAMETERS

[75] Inventor: Pierre Sarbach, Echallens, Switzerland

[73] Assignee: Baumann & Haldi S.A., Fleurier, Switzerland

[21] Appl. No.: 594,804

[22] Filed: Jan. 31, 1996

[30] Foreign Application Priority Data

Feb. 4, 1995 [CH] Switzerland ............ 00 295/95-0

[51] Int. Cl.⁶ ........................... A61B 5/02
[52] U.S. Cl. ........................... 128/670; 128/903
[58] Field of Search ............. 128/670, 668, 128/707, 710, 903, 905; 340/825.2, 825.21

[56] References Cited

U.S. PATENT DOCUMENTS

| | | |
|---|---|---|
| 3,972,320 | 8/1976 | Kalman . |
| 4,625,733 | 12/1986 | Säynäjäkangas ............ 128/903 |
| 4,952,928 | 8/1990 | Carroll et al. ............ 128/903 |
| 5,012,411 | 4/1991 | Policastro et al. ............ 128/710 |
| 5,036,869 | 8/1991 | Inahara ............ 128/903 |
| 5,157,604 | 10/1992 | Axford et al. ............ 128/903 |
| 5,400,794 | 3/1995 | Gorman . |
| 5,464,021 | 11/1995 | Birnbaum ............ 128/903 |

FOREIGN PATENT DOCUMENTS

| | | | |
|---|---|---|---|
| 0117330 | 9/1984 | European Pat. Off. ............ 128/707 |
| 2259772 | 3/1993 | United Kingdom ............ 128/903 |
| 9118550 | 12/1991 | WIPO . | |

OTHER PUBLICATIONS

Data Networks, Second Edition, Prentice Hall, New Jersey, 1992.

Proceedings of the Seventh Annual Conference of the IEEE/EMB Society, Sep. 30, 1985, Chicago pp. 1205–1210, J.H. Schild et al, A Low–Power Multichannel Biotelemeter Jul. 23, 1996.

Primary Examiner—Angela D. Sykes
Assistant Examiner—Bryan K. Yarnell
Attorney, Agent, or Firm—Sughrue, Mion, Zinn, Macpeak & Seas

[57] ABSTRACT

The invention concerns a system for measuring and displaying physiological parameters. It comprises, on the one hand, a sensor or sensors and a measuring device attached to the body, and on the other hand, a separate display device, for example a digital watch attached to the wrist, receiving from the measuring device the parameters to be displayed in the form of digitalised radio signals. A first application example concerns the measurement of the ECG signal and the display of parameters relating to the heart. A second example concerns the measurement of blood sugar levels and the display of insulin doses to be injected, if required.

13 Claims, 4 Drawing Sheets

AUTONOMOUS SYSTEM FOR MEASURING, PROCESSING AND TRANSMITTING ESSENTIALLY PHYSIOLOGICAL PARAMETERS

BACKGROUND OF THE INVENTION

The present invention concerns an autonomous system for measuring, processing, and transmitting essentially physiological parameters. It is increasingly important in the treatment of numerous illnesses and in the practice of several sports to know accurately certain physiological parameters of an individual, such as the heartbeat rate, blood pressure, blood sugar level, as well as parameters connected to the sporting activity, such as the speed or the power developed by the individual. To this end, numerous types of light sensors which are easy to attach to the wearer have been developed over recent years, ranging from simple electric contacts for taking an electrocardiogram (ECG), to complex sensors directly incorporated for example in silicon chips.

Most of these sensors provide electric signals in connection with the parameter(s) to be measured and carry numerous useful data. For example, for an electrocardiogram, there will be characteristic pulses whose frequency directly reflects the heartbeat rate. However, a deeper analysis of the shape of these pulses could provide additional information on certain malfunctions and could thus enable certain cardiac failures to be prevented.

The processing of the signals provided by the sensors presents no problem in the case where the individual can be connected to a fixed installation, for example when the person is confined to bed, or is only connected to a fixed measuring installation for a relatively short period of time. A design of this type corresponds for example to the device disclosed in patent application GB-A-2 259 772 in which detecting apparatus worn by several users transmit biological data to a central unit via radio waves. It is completely different if long term monitoring is desired and/or if the person has to maintain total mobility, while still being able to have easy access to read the desired parameters. At the present time, it is possible to make small autonomous signal processing devices capable of being attached to the individual, for example directly onto the abdomen by means of a belt or straps. It is easy to understand in the case cited above that, in order to be easily read, the means for displaying the parameters must be separated from the signal processing system. A wire connection is also delicate in that this wire may easily break when the person moves.

An interesting example of wireless connection is given by certain heartbeat rate reading systems used for training high level sportspersons. These systems comprise a belt including ECG signal sensors and a simple signal shaping device generating pulses at the heartbeat rate. These pulses are then transmitted without wire by all or nothing modulation of a radio signal to a device for receiving, processing and measuring these signals, enabling the heartbeat rate to be computed and displayed. The receiving and display device may for example be incorporated in a watch attached to the wrist, or placed on the handlebar of a bicycle, in the manner most suited to the type of use. It may then be combined with other functions, particularly time or stopwatch functions. A device of this type is for example disclosed in patent application FR-A-2 685 189. The first significant drawback of the known systems lies in the fact that the measuring is carried out at the receiving device. Thus any interference in the radio connection may introduce measuring errors and an erroneous display of the heartbeat rate. The second significant drawback is the limitation of a system of this type. In its present design it allows only the heartbeat rate to be measured, since it merely transmits pulses at this rate. However, as seen above, certain applications require a deeper analysis of the ECG signal, or even the analysis of parameters provided by other types of sensors. A final important point consists of reducing as much as possible the energy consumption, particularly as regards the receiving and display device, which is usually supplied with power by battery and must be as autonomous as possible, especially if it is also used as a watch as stated above.

SUMMARY OF THE INVENTION

The present invention provides original and effective solutions in this regard. It concerns a system for measuring and displaying at least one essentially physiological parameter by means of at least one sensor worn by an individual, said sensor providing signals representative of said parameter, comprising on the one hand an autonomous processing device which is attached to said sensor and provided with means for measuring, storing and identifying said signals and, on the other hand, a separate display device connected to the processing device by wireless communicating means, characterized in that said processing device further comprises coding means arranged so as to generate sequences of radio signals at the terminals of a transmitting coil, one of said sequences constituting an address enabling the transmitting processing device to be identified, the other sequences being representative of each category of measurement and its result, and in that the separate display device comprises a receiving coil, signal amplifying and shaping means at the terminals of said receiving coil and means for decoding these signals arranged so as to restore and to display the data transmitted by said processing device only if a determined address has previously been identified.

DESCRIPTION OF PREFERRED EMBODIMENTS

Figure 1:
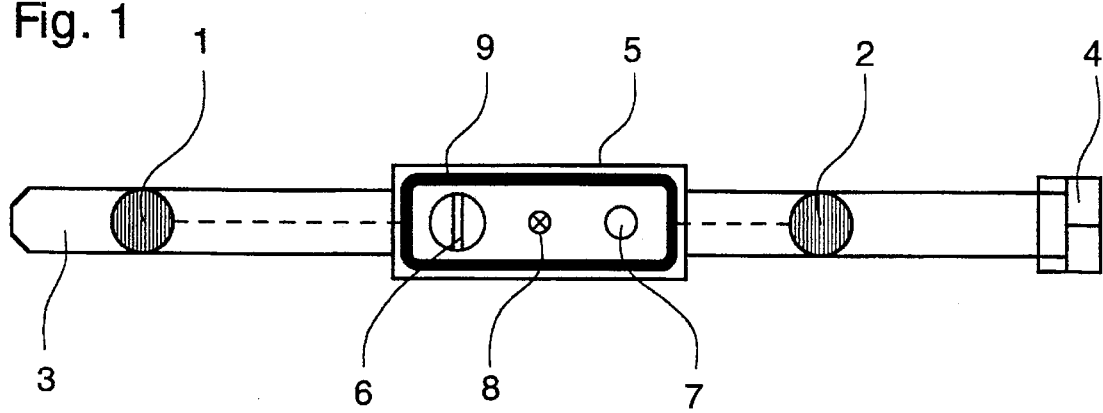
FIG. 1 shows schematically by way of example the processing device worn by the individual and forming one of the constituent components of the system according to the invention.

FIG. 1 shows schematically by way of example the processing device worn by the individual and forming one of the constituent components of the system according to the invention. For example the sensor or sensors 1, 2 may be mounted on a belt 3 able to be fastened around the waist either by means of a fastening buckle 4, or by a Velcro type fastening. In the case shown, sensors 1 and 2 are simple electric contacts for example in conductive rubber enabling the ECG signal to be detected. These sensors are directly connected to the autonomous signal processing device 5, which is also fixed onto the belt. This processing device 5 typically comprises an electronic circuit which will be described in detail below, a battery with an access system 6 enabling the latter to be changed easily, a push button or a switch 7 enabling the device to be set into operation or reinitialised, and display means, which can be, as in this case, a single LED diode 8, enabling the correct operation of the device to be monitored. Finally the device comprises a transmitting coil 9 enabling the radio connection with the display means to be assured.

Figure 2:
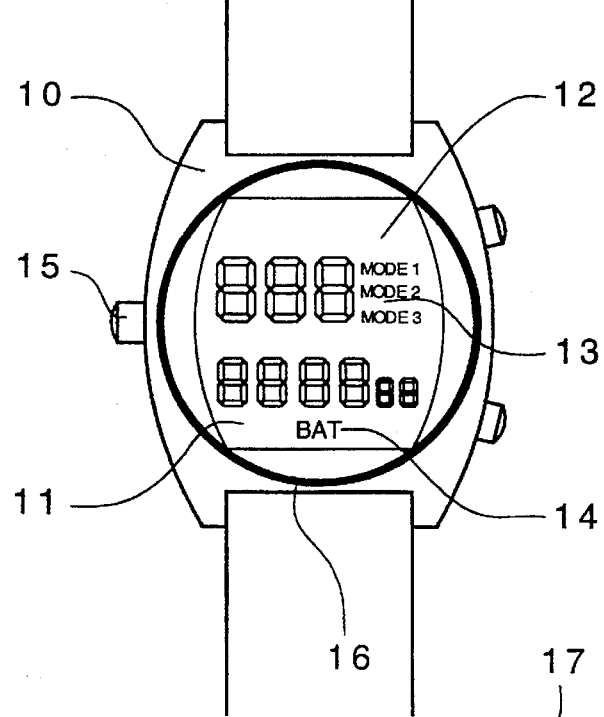
FIG. 2 shows schematically by way of example a display device of the system according to the invention.

These display means appear are shown in our example of FIG. 2 in the form of a digital watch 10 comprising a conventional hour, minute and second display 11, and a special display 12 of the parameters measured by processing device 5. The display may also comprise flags and symbols corresponding to the parameters to be displayed 13 or to certain special circumstances 14, for example the end of the batteries' life. The watch also comprises push buttons 15 enabling the different functions to be called and, if required, corrected, and a receiving coil 16 which enables the radio signals from processing device 5 to be received. The watch may also comprise a buzzer enabling the wearer's attention to be attracted in case of need. This function is not shown insofar as it is perfectly known to persons skilled in the art.

It is to be noted that the display means may also be arranged so as to be able to be attached to a support other than the person himself, for example to the handlebar of a bicycle in the case of a cyclist, or close to the head of a bed in the case of a bedridden person. In the latter case, the display means may be used with an assistance or alarm system enabling the attention of the personnel to be attracted in the event of a problem. However, these are particular applications which do not fundamentally modify the operation of the system.

Figure 3:
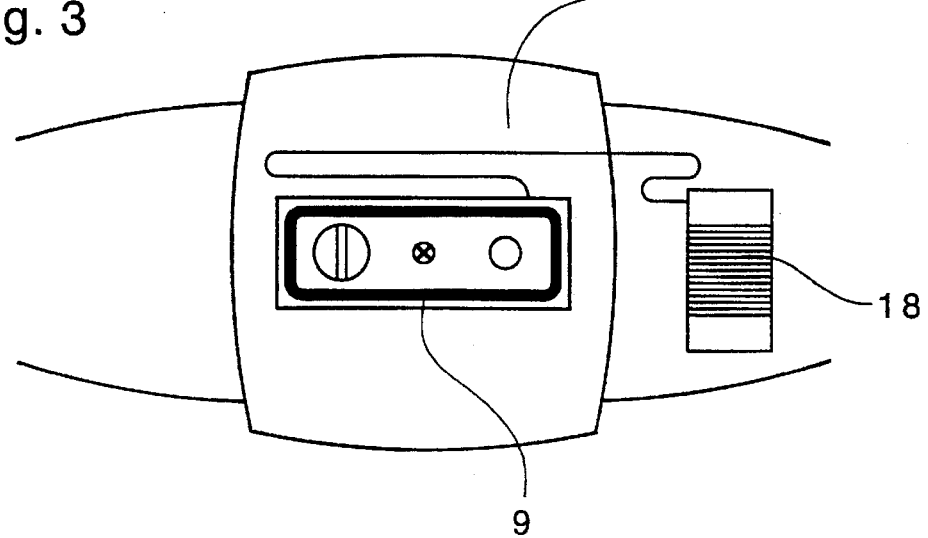
FIG. 3 shows another embodiment of the measuring device worn by the individual.

Processing device 5 may also be attached in other ways, for example as shown in FIG. 3 by means of an armband 17 on the upper arm, and be used with other types of sensor fixed close by, for example a temperature sensor 18. Other sensors, not attached to the user, may be used, such as a sensor for determining the speed or the power developed by an individual. There presently exist sensors capable of measuring certain parameters of the blood, for example the sugar level. The measurement of this parameter is essential in the treatment of diabetes and it would be possible to display this value and to determine when the wearer needs insulin and in what quantity, by using this type of sensor with the system according to the invention.

Figure 4:
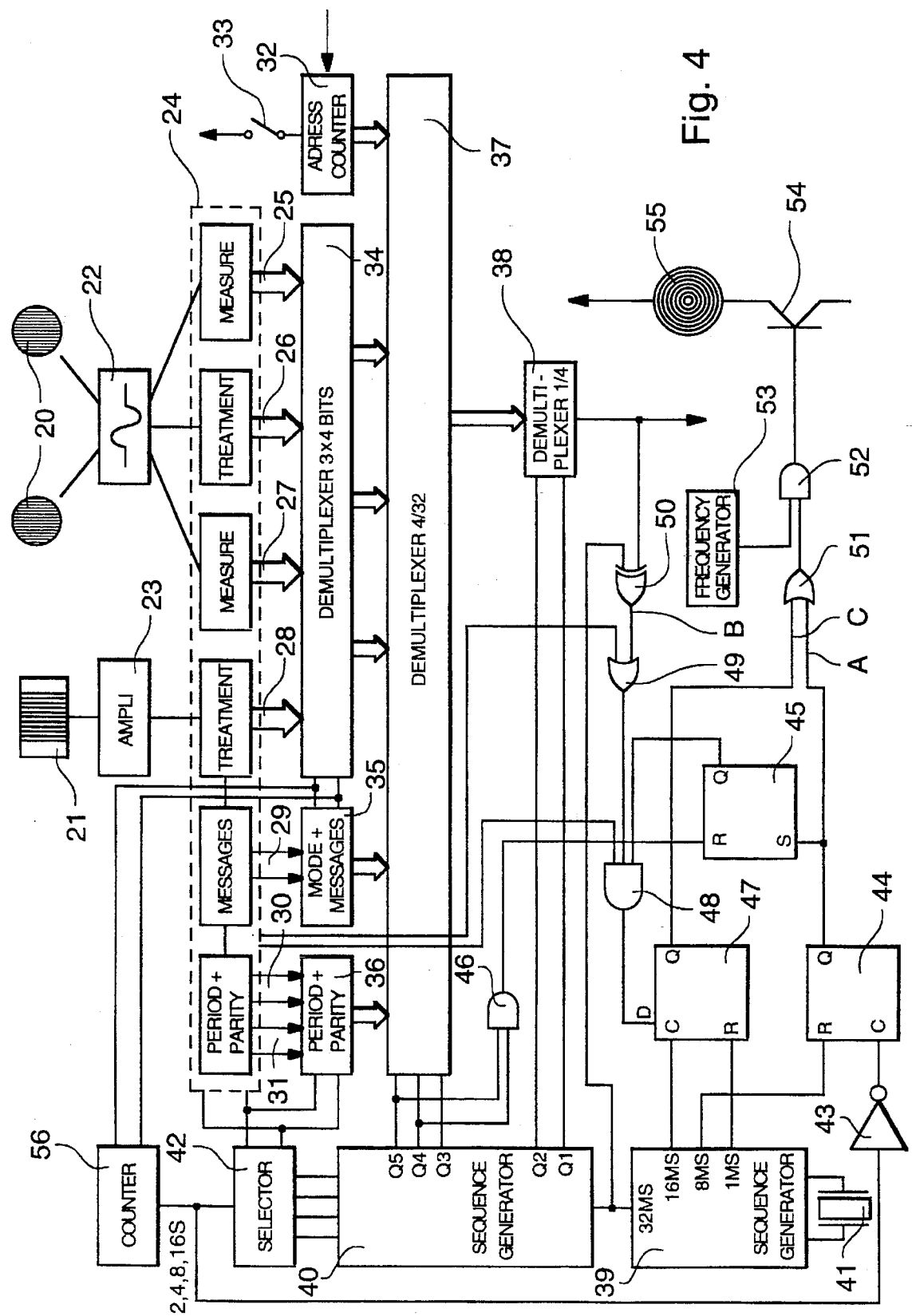
FIG. 4 shows by way of example the block diagram of a processing device according to the invention.

FIG. 4 shows byway of example the block diagram of a processing device according to the invention. This processing device may use several types of sensors, for example an ECG signal sensor 20 and a temperature sensor 21. Each of these sensors is connected to an amplifier 23 and signal setting circuit 22 which are in turn connected to means 24 for processing and measuring these signals. These means 24 provide binary data equally able to relate to the results of these measurements, as to their identification or their classification. Thus, from a single sensor, for example ECG signal sensor 20, processing means 24 could determine several parameters. First the instant heartbeat rate 25, the average of the latter over for example 100 beats 26, and the variations in the latter expressed in increasing or decreasing percentages 27. There are thus three distinct parameters determined from a same sensor. One may also have one or more determined parameters from one or more additional sensors, typically sensor 21 which is connected to amplifier 23 and which determines parameter 28. Parameters 25, 26, 27 and 28 are all represented in the form of binary data of 3*4 bits, representing four decimal ciphers.

Processing means 24 are shown here very schematically in the form of relatively simple wired logic. In practice, microprocessor controlled programmed logic is preferably used. There presently exists a whole range of very low consumption microprocessors capable not only of performing the aforementioned different measuring and measurement processing operations, but also of performing the classification of these measurements and of generating monitoring and error signals. In our example these error messages are represented by 2 bits allowing 4 combinations, each combination corresponding to a particular message, end of battery life, poor contact, etc.. The processing means may also generate parity bits 30 enabling the correct compliance of received messages to be monitored. Finally, processing means 24 may be used to optimise the energy consumption of the device so as to obtain the highest level of autonomy possible. This consumption is largely determined by the consumption of the radio transmitter. This may be achieved by adapting the periods of time when this transmitter is switched on to strictly necessary requirements by ad hoc algorithms controlled by the processing means. In this case it is of course necessary to indicate to the display means the value of these periods when the transmitter is switched on. In our example, this period is represented by 2 bit data 31 corresponding to transmitting periods of 2, 4, 8 and 16 seconds.

From the data and other information provided by the processing means, it is a matter of creating a pulse train of fixed duration to be transmitted to the display device means. This pulse train is formed in the following manner:

| | |
|---|---|
| 1, 2, 3, 4 | address |
| 5, 6, 7, 8 | FIG. 1 |
| 9, 10, 11, 12 | FIG. 2 |
| 13, 14, 15, 16 | FIG. 3 |
| 17, 18 | mode |
| 19, 20 | messages |
| 21, 22 | period |
| 23, 24 | parity |

Each pulse train thus corresponds to data of 24 bits, namely 6 groups of 4 bits. The address enables the transmitter to be identified. In fact it is possible, in certain cases, that two transmitters are close to each other. It is thus important that the receiver can differentiate between the two transmitters. The first group corresponds to this address which is randomly fixed, for example, by a 4 bit counter 32 as a function of the period of time that a switch 33 is closed.

The next three groups correspond to the value of the parameter expressed in three figures. In order to avoid having pulse trains which are too long and of variable duration, the value of only one parameter is sent per pulse train. The different parameters, four in the case described, are selected in turn by processing means 24 via a demultiplexer 34.

The next group consists of 2 bits 29 corresponding to the selected mode or parameter. It is important that the display means know to which parameter the values transmitted by the processing means correspond. The two following bits correspond to special messages, alarm, end of battery life, etc.. These 4 bits are mixed by circuit 35.

The last group consists of 2 bits defining the transmission period determined by processing means 24. And the two last bits are parity bits enabling the transmission quality to be monitored. These 4 bits are mixed by circuit 36.

There are thus 6 groups of 4 bits. Each of these groups of 4 bits is selected in turn by a 4/32 demultiplexer 37, then each bit of the group is selected in turn by a 1/4 demultiplexer 38, so as to create a binary data series formed of a sequence of 24 bits.

In order to create this binary data series, a sequence generator 39, 40 controlled by a quartz 41 is used. The first part 39 of the sequence generator is a binary counter which generates the different signals necessary for the formation of the pulses. The second part 40 of this generator is a binary counter which generates the different signals necessary for controlling demultiplexers 37 and 38 (outputs Q1, Q2, Q3, Q4, Q5) so as to form the 24 bit pulse train forming the data to be transmitted to the display device. Furthermore, this counter 40 fixes 4 repetition periods of 2, 4, 8 and 16 seconds of the pulse trains able to be chosen by 1/4 selector 42 as a function of the period determined by processing means 24.

Figure 5:
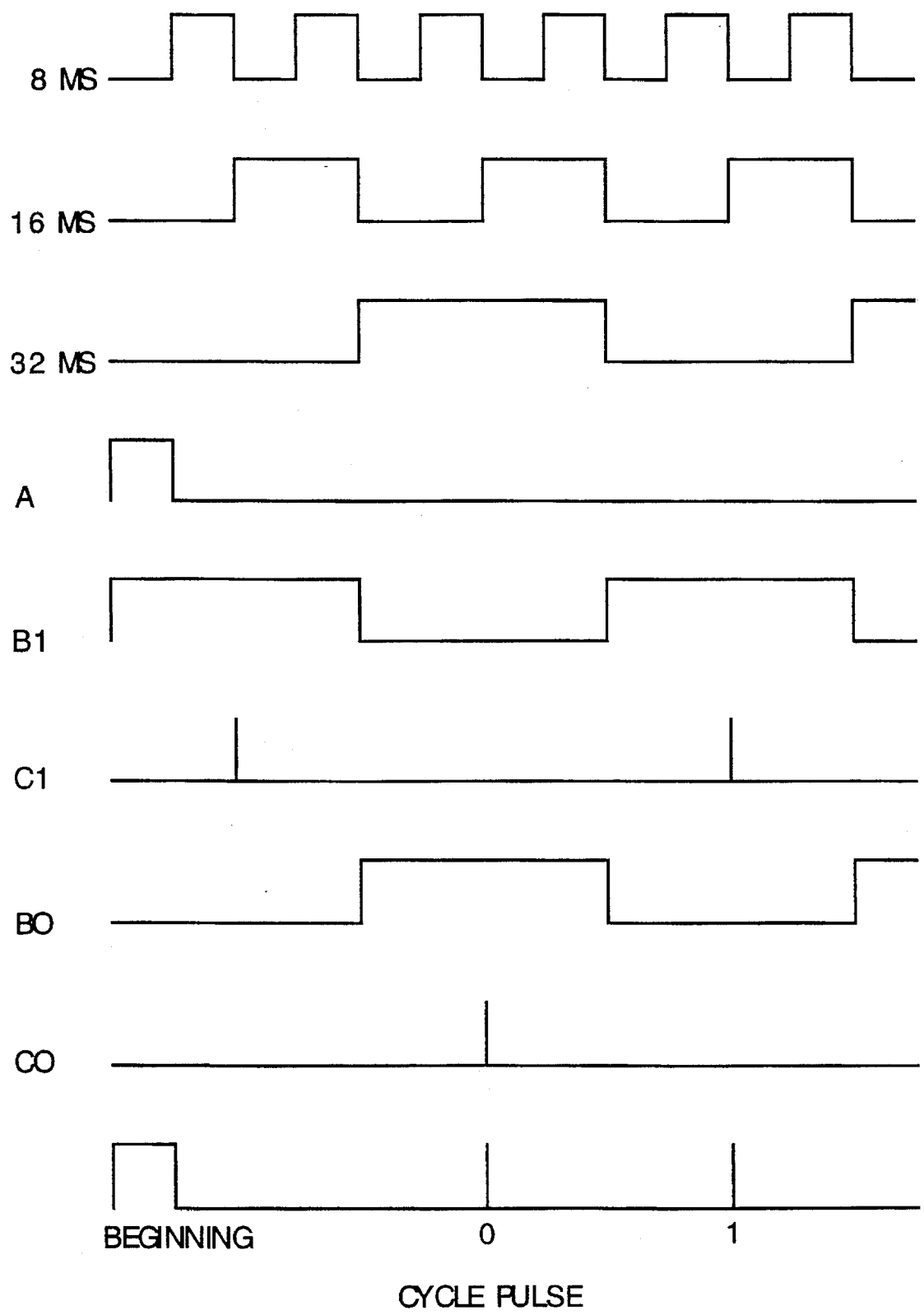
FIG. 5 shows the characteristic shape of the signals at certain points of the block diagram of FIG. 4.

The output signal of selector 42 is applied via an inverter gate 43 to the clock input of an D flip-flop 44 whose reset input is connected to the 8 millisecond output of counter 39. Thus D flip-flop 44 generates at its output Q a 4 millisecond pulse at the beginning of each transmission period. This output Q is connected to the set input of an D flip-flop 45 whose reset output is connected to the output of an AND gate 46 whose inputs are connected to outputs Q4 and Q5 of counter 40. Thus D flip-flop 45 passes to 1 during 24 input periods of counter 40, namely 760 milliseconds corresponding to the duration of each pulse train. Finally the clock input of D flip-flop 47 is connected to the 16 millisecond output of counter 39, while its reset input is connected to the 1 millisecond output of the same counter. D flip-flop 47 thus generates short pulses of 0.5 milliseconds as long as its input D is at 1. This input is connected to the output of a triple input AND gate 48. The first input is connected to the output of D flip-flop 45, so that these pulses can only be generated during the course of 24 periods fixed by this D flip-flop 45. The second input of gate 48 is connected via OR gate 49 to the output of an exclusive OR gate 50 one of whose inputs is connected to the 32 millisecond output of counter 39, the other input being connected to the output of demultiplexer 38 at which the data series representative of the data to be transmitted to the display means is generated. FIG. 5 gives the timing of the signals at points A, B and C.

The third input of gate 48 is connected to processing means 24 and enables input d of D flip-flop 47 to be blocked at 0, which may be considered as an ENABLE function which enables the generation of the short pulses to be suspended independently of the state of the output of demultiplexer 38. The second input of gate 49 is connected to processing means 24 and enables input D of the D flip-flop to be kept at 1, which may be considered as the inverse function enabling the generation of the short pulses to be maintained independently of output state of the output of demultiplexer 38. The uses of these ENABLE AND INVERSE ENABLE functions will be seen below after the description of FIG. 5. The outputs of D flip-flops 44 and 47 are connected to the inputs of an OR gate 51 at the output of which appears the short pulse train forming the complete data to be transmitted to the display device. The output of this gate goes to an input of an AND gate 52 whose second input is connected to the output of a 65 kHz frequency generator 53. The signal at the output of gate 52 is thus a 0.5 millisecond all or nothing modulated pulse at the frequency of 65 kHz and constitutes the low frequency radio signal which is transmitted to the exterior via an amplifier transistor 54 and transmitting coil 55.

Finally the output of selector 42 is connected to a counter-by-4 56 whose outputs Q1 and Q2 are connected to data selector 34 so as to select in turn parameters 25, 26, 27 and 28.

FIG. 5 shows the characteristic shape of the signals at certain points of the diagram of FIG. 4.

Thus the 8 millisecond, 16 millisecond and 32 millisecond outputs of counter 39 again appear. Output A corresponds to the beginning of cycle pulse at the output of D flip-flop 44. B1 and C1 give the configuration of the signals at points B and C when the output of demultiplexer 38 is at 1. One sees that the corresponding short pulses arrive while the 32 millisecond signal is at 0. B0 and C0 give the configuration of the signals at points B and C when the output of demultiplexer 38 is at 0. One sees that the corresponding short pulses arrive while the 32 millisecond signal is at 1. Thus the distribution of the short pulses inside the pulse train generated at the output of gate 51 is directly representative of the 0 and 1 sequence of data to be transmitted to the display means.

It can be noted that, during the pulse train, there is normally 1 short pulse per 32 millisecond period, and there are 24 short pulses per pulse train. By using the ENABLE function mentioned in FIG. 4, pulses can be suppressed if they are of no use. This suppression of pulses may be used for example if part of the data is unnecessary. For example if the value of the parameter to be displayed comprises only 2 figures, the pulses corresponding to the third figure can be suppressed and the latter can be switched off rather than displaying a 0. Likewise, if the processing device concerns only one parameter, the pulses relating to the mode can be suppressed, as can the mode display, and so on. By enabling the number of pulses per pulse train to be reduced, this combination enables the system to be simplified, while reducing the energy consumption and increasing the autonomy of the processing device.

Conversely, by means of the INVERSE ENABLE function, 2 short pulses can be generated per 32 millisecond period, which may be interpreted as a particular case, for example if the value of the parameter to be displayed exceeds the display capacity.

Figure 6:
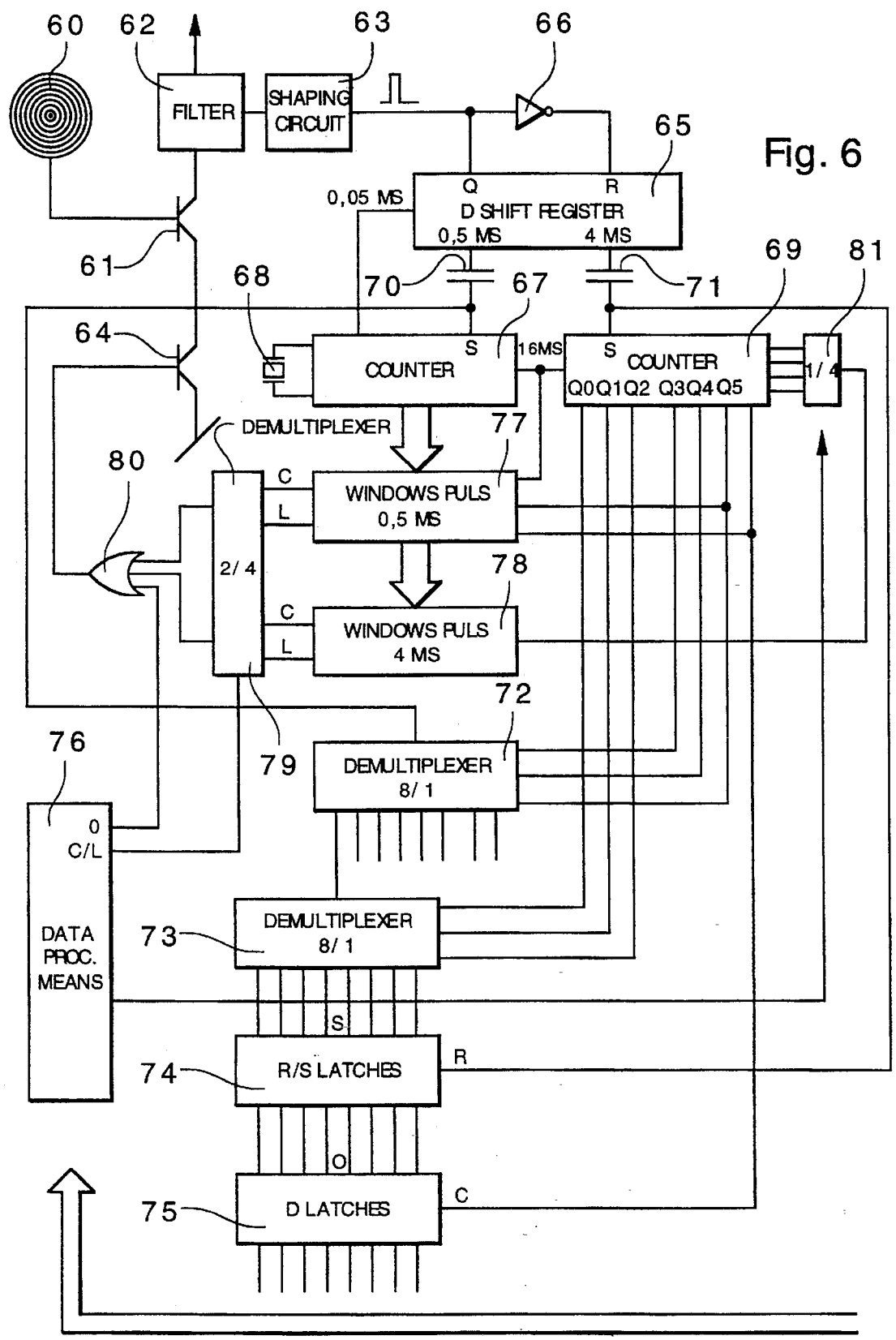
FIG. 6 shows by way of example the block diagram of the display device decoding means enabling the data sent by the processing device to be restored.

FIG. 6 shows byway of example the block diagram of the display device decoding means enabling the data sent by the processing device to be restored. A receiving coil 60 is connected to a transistor amplifier 61 whose collector is connected to a filter 62 which is connected to a shaping circuit 63. This combination of circuits enables the pulse trains transmitted by the transmitting coil to be restored when the receiving coil is situated in the field of said transmitting coil. The transmitter of transistor 61 is connected to a switching transistor 64 enabling the input amplifier to be shut down. The pulse trains at the output of shaping circuit 63 are applied to the D input of a D shift register 65, and via a inverter gate 66 to the reset input 64 of this shift. The clock input of this shift is connected to an output of a sequence generator comprising a binary counter 67 having an output period of 16 milliseconds, controlled by a quartz 68 and connected to a second binary counter 69. This configuration is not unlike the sequence generator of FIG. 4, and is effectively used to restore the data transmitted by the processing device. Shift register 65 is arranged so as to sort the input pulses according to their length. In the absence of any pulses, this shift is kept at 0. When a pulse appears, the different stages of the shift register rotate in turn for as long as the pulse is maintained. When the pulse lasts 0.5 milliseconds or more, the 0.5 millisecond output passes to 1. This output is connected by a capacitor 70 to a synchronising input of counter 67 so as to synchronise the output of this counter in phase with the short pulses of 0.5 milliseconds representative of the 0 and 1 sequence of data transmitted by the processing device. If the pulse lasts 4 milliseconds or more, the 4 millisecond output of shift register 65 passes to 1. This output is connected by a capacitor 71 to a synchronising input of counter 69 so as to synchronise the output of this counter in phase with the pulse train cycle transmitted by the processing device. Thus when these pulse trains are correctly received, it can be said that the display device sequence generator operates in synchronisation with the processing device sequence generator and it is thus possible to sort the short pulses as a function of their distribution in time. It is to be noted that, once the synchronisation is established, the latter is maintained even during a temporary disappearance of the radio connection because of the precision of the quartz which control these two generators.

In order to sort the short pulses, the latter are connected to the input of an 8/1 demultiplexer 72 whose selection inputs are connected to outputs Q3, Q4 and Q5 of counter 69. Demultiplexer 72 enables the pulse train to be cut into 6 series of 8 pulses. Why series of 8 pulses when the pulse train is normally formed of 24 pulses representing 6 groups of 4 bits? It must be recalled that each bit offers 2 pulse possibilities, one corresponding to state 0 and the other to state 1. Thus when one speaks of series of 8 pulses, one means 8 potentially possible pulses. In the case of normal binary data, in reality there will only be 4 pulses since one cannot simultaneously have a 0 and a 1 for a same bit. However, by using the ENABLE function of FIG. 4, the number of pulses may fall to 0, or pass to 8 by series if the INVERSE ENABLE function is used.

In order to facilitate the explanation, we will describe the way in which one of these series of 8 potential possible pulses is sorted, it being understood that the same arrangement is repeated six times, once for each serie. The first output of demultiplexer 72 is connected to the input of a second 8/1 demultiplexer 73 whose selection inputs are connected to outputs Q0, Q1 and Q2 of counter 69. Thus each serie of 8 potential possible pulses is divided into 8 time periods, which enables each pulse to be directed to a different output as a function of the order in which it arrives. The 8 outputs of demultiplexer 73 are connected to the 8 set inputs of a group of R/S latches 74 whose outputs are connected to the 8 D inputs of a group of D latches 75. At the beginning of a transmission cycle, R/S latches 74 are reset at 0 by the synchronising pulse supplied by capacitor 71, which is connected to the reset input of these latches. These R/S latches then pass to 1 as long as a pulse appears in the period of time allotted to them. At the end of the pulse train, the distribution of the R/S latches which have not remained at 0 and of those which have passed to 1 restore the data which has been transmitted by the processing device. The state of the R/S latches is stored in the D latches at the end of the transmission cycle. To this end, the clock input of these D latches is connected to output Q6 of counter 69. The data at the output of the 6 groups of D latches (only one of which is shown) is transmitted to data processing means 76, said means being arranged so as to control the display of all or part of this data, and to control other functions, for example to modify the length of the receiving cycle as a function of the "period" data received from the processing device. To this end an output of these means 76 is connected to the control inputs of a selector enabling one of the 4 available periods of 2, 4, 8 or 16 seconds to be selected.

Finally, one of the crucial problems, particularly as regards the display device, is the energy consumption upon which the autonomy of the device is conditioned. One of the components which uses the most energy is the input amplifier, since, in order to have a good level of sensitivity, it must be biased in class A. However, this amplifier is only needed for a very short while at the moment when a pulse ought to appear, to see whether this pulse is present or not. It is possible, by means of the sequence generator, to generate short term windows synchronous with the pulses to be received and only to set the amplifier into operation during these windows. A first circuit 77 connected to outputs of counters 67 and 69 enables windows synchronous with the short 0.5 millisecond pulses to be generated. This circuit 77 has 2 outputs, one output C corresponding to the short windows, and the other L to the longer windows. A second circuit 78 connected to the output of period selector 77 enables windows synchronous with the 4 millisecond long pulses from the beginning of the transmission cycle to be generated. This circuit 78 has 2 outputs, one output C corresponding to the short windows and the other L to the longer windows. Outputs C and L of circuits 77 and 78 are connected to the inputs of a 2/4 selector enabling either the short windows or the long windows to be selected, at the command of processing means 76. These processing means 76 also enable the input amplifier to be kept at will in permanent operation. To this end, processing means 76 are connected to an input of an OR gate 79 which receives at its two other inputs the signals corresponding to the windows generated by circuits 77 and 78. The output of gate 79 controls transistor switch 64 and enables the input amplifier to be set into operation permanently or during short or long windows at the command of the data processing means.

I claim:

1. A system for measuring and displaying at least one physiological parameter by means of at least one sensor worn by an individual and providing signals representative of said parameter, said system comprising: on the one hand an autonomous processing apparatus which is attached to said sensor and provided with a plurality of means for measuring, for storing, for identifying and for binary coding said signals, said binary coding means being arranged so as to generate pulse trains of binary sequences of radio signals at terminals of a transmitting coil for transmitting the radio signals, one of said sequences constituting an address enabling a transmitting processing device to be identified, others of said sequences being representative of data constituted by a measurement and its result; and, on the other hand, a separate display device connected to the processing apparatus by wireless communicating means, said separate display device comprising a radio signal-receiving coil, signal amplifying and shaping means at terminals of said receiving coil, and means for decoding the signals, characterized in that the decoding means comprises a sequence generator arranged so as to open detecting windows synchronous with the pulse trains transmitted by the processing device, and to restore the binary sequence representative of the transmitted data as a function of distribution of said pulses in said detecting windows, in that the signal amplifying means at the terminals of the receiving coil are set into operation only during occurrence of said detecting windows, so as to reduce energy consumption, and in that the data transmitted by said processing device are restored and displayed only if a determined address had previously been identified.

2. A system according to claim 1 characterized in that the binary coding means comprises a sequence generator supplying short pulse trains to terminals of an all or nothing radio signal modulator.

3. System according to claim 1 characterized in that said identifying means are arranged so as to determine said address randomly when the processing device is switched on.

4. System according to claim 1, characterized in that the processing device measuring means are arranged so as to fix the period of an emitting start of the radio signal sequences generated by the coding means, the value of this period being represented in the form of a binary code incorporated in said radio signal sequences.

5. System according to claim 4, characterized in that the display device decoding means comprise a sequence generator arranged so as to open detecting windows synchronous with the pulse trains transmitted by the processing device, and to restore a binary sequence 0 and 1 representative of the transmitted data as a function of the distribution of said pulses in said detecting windows; and in that the display device decoding means sequence generator is arranged so as to adapt the detecting period as a function of the binary code corresponding to this period transmitted by the processing means.

6. System according to claim 1, characterized in that the processing device comprises means for generating monitoring and error signals at the address of the display device in the form of binary codes incorporated via coding means in the radio signal sequences at the terminals of the transmitting coil.

7. System according to claim 1, characterized in that at least one other sensor enables signals representative of a non-physiological parameter to be supplied.

8. System according to claim 7, characterized in that the non-physiological parameter are selected from among the speed or the power developed by the individual.

9. A system for measuring and displaying at least one physiological parameter by means of at least one sensor worn by an individual and providing signals representative of said parameter, said system comprising on the one hand an autonomous processing apparatus which is attached to said sensor and provided with means for measuring, for storing, for identifying and for binary coding said signals, said binary coding means including a first sequence generator to generate pulse trains of binary sequences of radio signals at terminals of a transmitting coil, for transmitting the radio signals one of said sequences constituting an address enabling a transmitting processing device to be identified, others of said sequences being representative of data constituted by a measurement and its result and, on the other hand, a separate display device connected to the processing apparatuses by wireless communicating means, said separate display device comprising a radio signal-receiving coil, signal amplifying and shaping means at terminals of said receiving coil, and means for decoding the signals, characterized in that the decoding means comprises a second sequence generator arranged so as to open detecting windows synchronous with the pulse trains transmitted by the processing device, and to restore the binary sequence representative of the transmitted data as a function of distribution of said pulse trains in said detecting windows, in that the data transmitted by said processing device are restored and displayed only if a determined address had previously been identified and in that the decoding means is arranged so as to generate an initialization sequence of limited duration able to be locked in by an external command, said initialization sequence enabling on the one hand the second sequence generator to be synchronized with the first sequence generator, and on the other hand to store the address of said processing device.

10. A system for measuring and displaying at least one physiological parameter by means of at least one sensor worn by an individual and providing signals representative of said parameter, said system comprising on the one hand an autonomous processing device which is attached to said sensor and provided with means for measuring, for storing, for identifying and for coding said signals, said coding means being arranged so as to generate pulse trains of binary sequences of radio signals at terminals of a transmitting coil, one of said sequences constituting an address enabling a transmitting processing device to be identified, the other sequences being representative of data constituted by a measurement and its result and, on the other hand, a separate display device connected to the processing device by wireless communicating means, said separate display device comprising a receiving coil, signal amplifying and shaping means at terminals of said receiving coil, and means for decoding the signals, characterized in that the decoding means comprises a sequence generator arranged so as to open detecting windows synchronous with the pulse trains transmitted by the processing device, and to restore the binary sequence representative of the transmitted data as a function of the distribution of said pulses in said detecting windows, in that the data transmitted by said processing device are restored and displayed only if a determined address had previously been identified and in that said decoding means is arranged so as to generate a reinitialization sequence of limited duration when signal reception becomes insufficient, this reinitialization sequence enabling said sequence generator to be resynchronized with a processing device sequence generator corresponding to the stored address.

11. System according to claim 1, characterized in that the processing apparatus measuring, storing and identifying means are arranged so as to measure and store the results of measuring several parameters, and to identify the parameter concerned in the form of a binary code incorporated via coding means in the radio signal sequences at the terminals of the transmitting coil.

12. System according to claim 11, characterized in that the coding means are arranged so as to generate, in a cyclical manner at the terminals of the transmitting coil, sequences of signals corresponding successively to each of the measured parameters, identified by their respective codes.

13. System according to claim 12 characterized in that the display device comprises means for selecting the parameter to be displayed in response to an external command, said selecting means being arranged so as to synchronize with the radio signal sequence comprising the code corresponding to the selected parameter.

* * * * *